United States Patent
Zhang

(10) Patent No.: US 10,658,692 B1
(45) Date of Patent: May 19, 2020

(54) BIOLOGICAL BATTERY AND BIOLOGICAL CATHODE

(71) Applicant: Pei Zhang, Malden, MA (US)

(72) Inventor: Pei Zhang, Malden, MA (US)

(*) Notice: Subject to any disclaimer, the term of this patent is extended or adjusted under 35 U.S.C. 154(b) by 186 days.

(21) Appl. No.: 15/077,901

(22) Filed: Mar. 22, 2016

Related U.S. Application Data

(63) Continuation-in-part of application No. 14/323,260, filed on Jul. 3, 2014, now abandoned.

(60) Provisional application No. 61/841,847, filed on Jul. 1, 2013.

(51) Int. Cl.
| | | |
|---|---|---|
| *H01M 8/16* | (2006.01) | |
| *C12M 1/00* | (2006.01) | |
| *C12M 1/42* | (2006.01) | |
| *H01M 12/08* | (2006.01) | |
| *H01M 4/90* | (2006.01) | |
| *H01M 4/86* | (2006.01) | |

(52) U.S. Cl.
CPC .............. *H01M 8/16* (2013.01); *C12M 35/02* (2013.01); *C12M 43/08* (2013.01); *H01M 4/9008* (2013.01); *H01M 4/9075* (2013.01); *H01M 12/08* (2013.01); *H01M 2004/8689* (2013.01)

(58) Field of Classification Search
CPC ...... H01M 8/16; H01M 4/9075; H01M 12/08; C12M 35/02; C12M 43/08
USPC .......................................................... 429/2
See application file for complete search history.

(56) References Cited

U.S. PATENT DOCUMENTS

| | | | | |
|---|---|---|---|---|
| 5,316,871 A | * | 5/1994 | Swathirajan | C25B 9/10 429/492 |
| 8,642,308 B1 | * | 2/2014 | Atanassov | C12N 9/0006 435/181 |
| 2003/0091889 A1 | * | 5/2003 | Sotomura | H01M 12/06 429/405 |
| 2010/0224246 A1 | * | 9/2010 | Tender | H01M 8/0606 136/256 |
| 2011/0151544 A1 | * | 6/2011 | Lovley | C12N 1/20 435/245 |
| 2011/0236769 A1 | * | 9/2011 | Xie | B82Y 30/00 429/401 |
| 2011/0315560 A1 | * | 12/2011 | Rabaey | C02F 1/4618 205/344 |
| 2012/0288898 A1 | * | 11/2012 | Lovley | C12P 7/16 435/92 |
| 2012/0292187 A1 | * | 11/2012 | Kim | B01D 61/44 204/527 |

OTHER PUBLICATIONS http://www.fuelcellstore.com/vulcan-xc-72r accessed on Nov. 27, 2017.*

* cited by examiner

*Primary Examiner* — Cynthia H Kelly
*Assistant Examiner* — Rashid A Alam

(57) ABSTRACT

Biological material is used to build up biological cathode electrodes (biological cathode) and biological batteries, particularly biological metal air batteries as well as biological flow battery. A biological battery system includes a reaction vessel, a medium, a conductive anode and a biological cathode electrode. The biological cathode has a conductive support layer, a polymeric binding layer disposed between the conductive support layer and a contact layer. The contact layer being configured to be in electrical contact with biological components in the medium or being deposited with biological components. When the reaction vessel is open to an ambient air, the biological components accept electrons from the cathode.

3 Claims, 5 Drawing Sheets

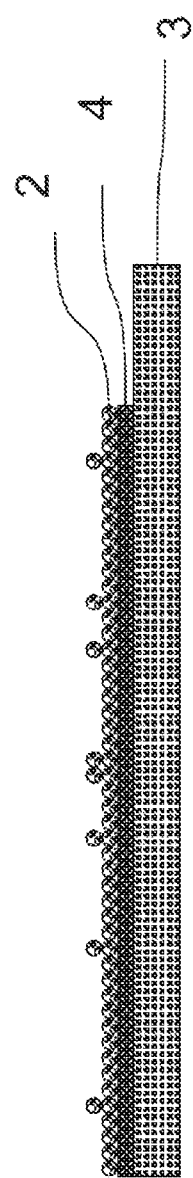

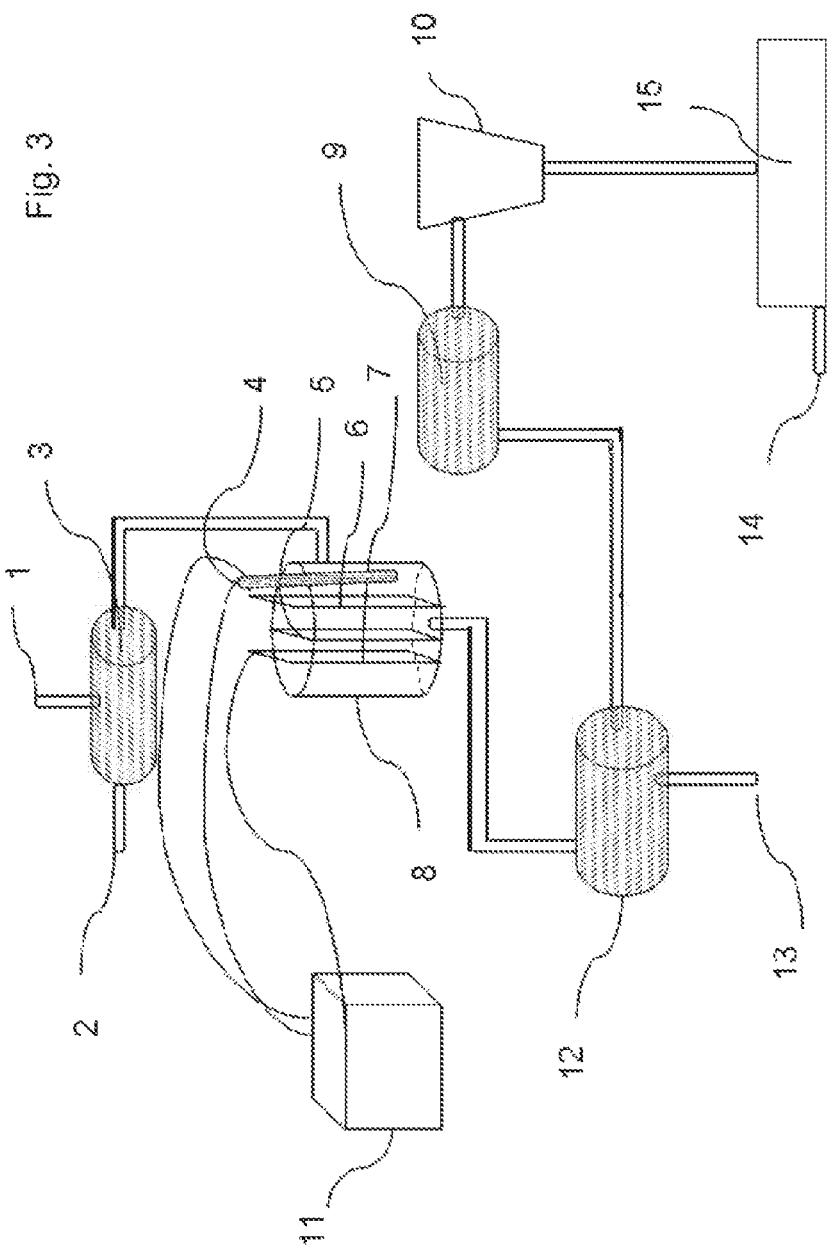

Fig. 4

| Author and year | Current density (A/m2) | Duration during testing (day) | Cathode material | Polarization method | Culture | Lowest Polarization potential vs. SHE(V) |
|---|---|---|---|---|---|---|
| Bergel et al, 2005 | 0.46 no control | 12 | Stainless steel | Constant Polarization | Mix culture | -0.156 |
| Erable B., Bergel et al. 2010 | 0.6 no control | NA | Graphite felt (no collector) | Constant Polarization | Mix culture | -0.001 |
| Rabaey et al. 2008 | 0.37 vs. control | Not indicated | Stainless steel | Polarization curve (1mV/s) | Pure culture | -0.32 |
| Vandecandelaere et al. 2008 | 0.50 no control | Not indicated | Stainless steel | Polarization curve | Pure culture | -0.001 |
| Pei Zhang et al, 2011(manuscript) | 0.92 vs. control | >11 | Graphite rod | Constant Polarization | Pure culture | -0.351 |
| Pei Zhang et al. 2012 | 7.5 vs. control | >11 | Carbon material | Constant Polarization | Pure culture | -0.351 |
| Pei Zhang et al | Expect > 7.5 vs. control | >11 | Compatible material | Constant Polarization | Pure culture | -0.351 |

BIOLOGICAL BATTERY AND BIOLOGICAL CATHODE

FIELD OF THE INVENTION

The invention concerns processes/methods of utilizing biological material to build up biological electrodes and biological/green batteries, particularly biological metal-air batteries as well as fuel cells. This invention also related to using biological material to produce useful anions, cations, acetic acid and other chemical compounds under certain electrochemical conditions.

BACKGROUND

Batteries and Metal-Air Batteries

A battery is a device consisting of one or more electrochemical cells convert stored chemical energy into electrical energy. Each cell contains a positive terminal, or cathode, and a negative terminal, or anode. Electrolytes allow ions to move between the electrodes and terminals to generate current, which flows out of the battery to perform work. According to a 2005 estimate, the worldwide battery industry generates US$48 billion in sales each year, with 6% annual growth. A metal-air battery is an electrochemical cell that uses an anode made from pure metal and a cathode utilizing ambient air as terminal electron acceptors, typically with an aqueous electrolyte. The theoretical specific energy densities for metal-air batteries are higher than for ion-based approaches, due to the use of atmospheric oxygen as the cathode, eliminating a traditional cathode structure (non-rechargeable). The common metal-air batteries include aluminum-air, lithium-air, zinc-air, calcium-air, magnesium-air, sodium-air, titaniumair, ion-air batteries. Following Lithium-air and Zinc-air batteries are elucidated as examples.

lithium-air batteries have been proposed as the next step in lithium battery architecture, due to the high specific energy density of lithium with respect to air (3840 mA·h/g)(Kumar 2010). At the cathode, electrons are oxidized by oxygen. Mesoporous carbon has been used as a cathode material with metal catalysts. Metal catalysts incorporated into the carbon electrode enhance the oxygen reduction kinetics and increase the specific capacity of the cathode (Daniel and Besenhard 1999). Manganese, cobalt, ruthenium, platinum, silver, or a mixture of cobalt and manganese are under consideration as metal catalysts. However the metals are expensive and less easy to access. Under some circumstances manganese catalyzed cathodes performed best, with a specific capacity of 3137 mA·H/g carbon, and cobalt catalyzed cathodes performed second best, with a specific capacity of 2414 mA·H/g carbon (Abraham and Jiang 2014).

Li-air cell performance is limited by the efficiency of reaction at the cathode, where most of the cell voltage drop occurs (Kraytsberg 2010). Part of the reason for the undeveloped potential of Li-air cells lays with the lack of a suitable catalyst for effecting the oxygen reduction. Multiple battery chemistries display varying electrochemical reactions at the cathode. The aprotic and aqueous electrolytes as the exact electrochemistry taking place in solid-state electrolytes is not well understood. The performance of li-air battery involves the interface of three phases: liquid electrolyte, solid cathode surface and oxygen gas. The oxygen-cathode interface is thought to be responsible for the rechargeability is the lack of thereof, of lithium-air batteries. Two factors play a crucial role: cathode catalyst composition and cathode porosity.

Li-air batteries are primarily motivated for the application of automotive power supplies because the high specific energy and volumetric energy densities of Li-air battery are the prime motivation for this design. Secondarily, Li-air batteries are attractive for applications demands high power density and light weight carriage, such as mobile devices.

Zinc-air batteries have received attention due to the potential for high energy densities. They are metal-air batteries powered by oxidizing zinc with oxygen from the air. These batteries have high energy densities and are relatively inexpensive to produce. Sizes range from very small button cells for hearing aids, larger batteries used in film cameras that previously used mercury batteries, to very large batteries used for electric vehicle propulsion. Zinc-air batteries can be used to replace now discontinued 1.35 V mercury batteries (although with a significantly shorter operating life), which in the 1970s through 1980s were commonly used in photo cameras. Possible future applications of this battery include its deployment as an electric vehicle battery and as a utility-scale energy storage system. As same as Lithium-air battery, the cathode oxidation reaction rate limits the performance of the zinc-air battery. Treasure metal catalysts are costive and some are causing environmental issues.

Tanaami et al. (U.S. patent application Ser. No. 13/624,938, filed Mar. 16, 2011, and hereby incorporated herein by reference in its entirety and made part of this application) discloses system and design of metal-air battery capable of obtaining large charge-discharge capacity than before. The patent is aiming to solve the problem that at the positive electrode, reaction rate is dominated by a diffusion speed of oxygen molecules and oxygen ions in the oxygen-occluding material. As a result, in the metal air battery equipped with the oxygen-occluding material at the positive electrode, the reaction rate of the battery reaction drops, and over potential increases. The patent try to solve the problem through the oxygen-containing species merely adsorbed at the surface of the mixture of the carbon material and the oxygen-storing material is not necessary to be diffused within the oxygen-storing material. However, the positive electrode, oxygen released from the oxygen occluding material is reduced to form oxygen ions, and form a metal oxide by bonding with the metal ions. Over the time, the metal oxide compounds are accumulated and clog the pore orifices causing termination of the Metal-air battery during discharge process.

In light of the foregoing, there is a need for a cost effective and practical method to solve the issue of the rate retardation of the oxygen oxidation on cathode surface due to slow diffusion of oxygen molecule and lack of catalysis. Also to avoid the accumulation of metal oxide on the electrode surface with high efficiency (90%) for higher efficiency and longer life time of the battery.

The principal object of the present invention is the provision of a process and/or methods for the production of a biological cathode electrode. A still further object of the present invention is the provision of a process of utilizing the biological material in electrode and battery building, especially cathode and metal-air batteries. The biological cathode catalyzes cathode oxygen oxidation reaction without adding expensive treasure metal as catalyst. Using the biological material to replace the caustic battery chemicals is safer and also friendly to environment and human health in long term. Yet another and more particular object of the present invention is the provision of a method, microorganisms, cathode electrode abiotic surface material, composition and apparatus involving biological surface coating cathode to prevent the accumulation of the metal oxide precipitations to enhance the efficiency and prolong the life time of the battery.

Fuel Cells

A fuel cell is a device that converts the chemical energy from a fuel into electricity through a chemical reaction with oxygen or another oxidizing agent (Khurmi 2013). Hydrogen is the most common fuel, but for greater efficiency hydrocarbons can be used directly such as natural gas and alcohols like methanol. Fuel cells are different from batteries in that they require a continuous source of fuel and oxygen/air to sustain the chemical reaction, however, in a battery the chemicals present in the battery react to generate electricity. Fuel cells can continuously produce electricity as long as fuels are supplied.

One example of fuel cell is zinc-air fuel cell. A mass of zinc particles forms a porous anode with an electrolyte. Oxygen in the air is reduced at the cathode and forms hydroxyl ions which migrate to anode, the zinc paste and form zincate, releasing electrons to travel to the cathode through external circuit. The zincate is decayed into zinc oxide and water into the electrolyte after the reaction. The water and hydroxyl from the anode are recycled at the cathode, so the water is not consumed. The reactions produce a theoretical 1.65 volts, but this is reduced to 1.35-1.4 V in available cells. Zinc-air fuel cells: the zinc is the fuel, the reaction rate can be controlled by varying the air flow, and oxidized zinc/electrolyte paste can be replaced with fresh paste.

Tanaami et al. (U.S. patent application Ser. No. 13/624,938, filed Mar. 16, 2011, and hereby incorporated herein by reference in its entirety and made part of this application) discloses system and design of metal-air battery capable of obtaining large charge-discharge capacity than before. The patent is aiming to solve the problem that at the positive electrode, reaction rate is dominated by a diffusion speed of oxygen molecules and oxygen ions in the oxygen-occluding material. As a result, in the metal air battery equipped with the oxygen-occluding material at the positive electrode, the reaction rate of the battery reaction drops, and over potential increases. The patent try to solve the problem through the oxygen-containing species merely adsorbed at the surface of the mixture of the carbon material and the oxygen-storing material is not necessary to be diffused within the oxygen-storing material. However, at the positive electrode, oxygen released from the oxygen containing material is reduced to form oxygen ions, and form a metal oxide by bonding with the metal ions. Over the time, the metal oxide compounds are accumulated and clog the pore orifices causing termination of the Metal-air battery during discharge process.

In light of the foregoing, there is a need for a cost effective and practical method to solve the issue of the rate retardation of the oxygen oxidation on cathode surface due to slow diffusion of oxygen molecule and lack of catalysis. Also to avoid the accumulation of metal oxide on the electrode surface with high efficiency (90%) for higher efficiency and longer life time of the battery.

The principal object of the present invention is the provision of a process and/or microorganism for the production of a biological cathode electrode. A still further object of the present invention is the provision of a process for using microorganisms to catalyze cathode oxygen oxidation reaction without adding expensive treasure metal as catalyst. Yet another and more particular object of the present invention is the provision of a method, microorganisms and apparatus involving biological surface coating cathode to prevent the accumulation of the metal oxide precipitations to enhance the efficiency and prolong the life time of the battery.

Microbial Fuel Cells

Microbial Fuel Cells (MFCs), which can harvest energy from microorganisms in the form of electricity, have gained worldwide interest. MFCs provide an energy alternative in the face of a wide-spread energy crisis and environmental problems. Developing MFC technology has become an urgent requirement for the sake of sustainability of our society. Energy generation in the process of biological oxygen demand (BOD) removal for waste treatment plant is a good example. As well, MFCs can be applied in occasions that battery or other power sources are not feasible, such as powering marine underwater devices etc.

A Microbial Fuel Cell converts chemical energy to electrical energy via electron exchange between two chambers, the anode chamber and the cathode chamber. In the anode chamber, oxygen-starved organic material (for example, wastewater) is oxidized by naturally occurring bacteria. This process releases protons and electrons. Electrons flow through a circuit to the cathode, where they combine with protons and terminal electron acceptors. Oxygen in air is commonly used as terminal electron acceptor for it has high oxidation potential. However the reduction of oxygen is critical and usually the limiting step for power generation. A sluggish oxygen reduction reaction (ORR) causes a large cathodic over-potential, i.e., about 80% of the overall loss in the cell. In previous research of MFC, enhanced performance has been achieved by utilizing specific microbial cultures on the anode side, catalyzing anode reaction and current generation. In particular, it has been shown that an increase in current density can be achieved by isolation of a particular variant of *G. sulfurreducens* named KN400 (Yi, 2009).

In addition, several other methods to improve the cathode performance include lowering the internal resistance of the cathode material, using more effective electron acceptors such as ferricyanide, potassium permanganate, manganese oxide in place of oxygen, and using a catalyst that efficiently enhances cathodic reactions at room temperature (Yang 2011). Chemical catalysts for the cathode, for example, plain Pt (Reimers, 2001) or Pt-coated carbon (Rozendal 2007) are expensive and only have limited life time (Schamphelaire 2008). Applying noble metals such as platinum in the cathode represents a capital challenge, not only because the substantial increase of the capital costs but also because of the sensitivity of the catalysts to poisoning issues in WC working conditions.

Using microorganisms to catalyze cathode-side reactions has been investigated. However, the performance is limited because of the lack of high-efficiency, functional microorganisms, low microorganism surface interaction with electrode material, medium composition, and other factors. Improved cathode systems and methods for improving cathode-side reactions are needed.

Akasaka et al. (U.S. patent application Ser. No. 12/355,170, filed Jan. 16, 2009, and hereby incorporated herein by reference in its entirety and made part of this application) discloses a pattern-forming material that contains a block copolymer or graft copolymer and forms a structure having micro polymer phases, in which, with respect to at least two polymer chains among polymer chains constituting the block copolymer or graft copolymer, the ratio between N/(Nc-No) values of monomer units constituting respective polymer chains is 1.4 or more, where N represents total number of atoms in the monomer unit, Nc represents the number of carbon atoms in the monomer unit, and No represents the number of oxygen atoms in the monomer unit.

Reppas et al. (U.S. Pat. No. 7,794,969, filed Apr. 13, 2010, and hereby incorporated herein by reference in its entirety and made part of this application) disclose methods and compositions for modifying photoautotrophic organisms as hosts, such that the organisms efficiently convert carbon dioxide and light into n-alkanes, and in particular the use of such organisms for the commercial production of n-alkanes and related molecules.

Ladisch et al. (U.S. patent application Ser. No. 10/875,990, filed Jun. 24, 2004, and hereby incorporated herein by reference in its entirety and made part of this application) disclose a bio-battery that includes a biomolecular energy source in a first electrode cell and a reducible substrate in a second electrode cell, the cells being in ionic communication by a proton exchange membrane.

Evans et al. (U.S. patent application Ser. No. 12/889,155, filed Sep. 23, 2010, and hereby incorporated herein by reference in its entirety and made part of this application) disclose a method of placing a bacterial cellulose matrix in a solution of a metal salt such that the metal salt is reduced to metallic form and the metal precipitates in or on the matrix, and a method for using the metallized bacterial cellulose in the construction of fuel cells and other electronic devices.

Swift et al. (U.S. patent application Ser. No. 12/468,108, filed May 19, 2009, and hereby incorporated herein by reference in its entirety and made part of this application) disclose a microbial fuel cell having multiple, substantially aligned, fibers whose outer surfaces receive a biofilm, the fibers within a conductive tube to form the anode, and the cell further having an anode chamber containing a fluid biomas and a cathode chamber containing an oxygenated fluid.

Han et al. (U.S. patent application Ser. No. 11/534,450, filed Sep. 22, 2006, and hereby incorporated herein by reference in its entirety and made part of this application) disclose a microfluidic device for electrochemically regulating the pH of a fluid comprising: a cathode substrate; an anode substrate facing the cathode substrate and forming a reaction chamber with the cathode substrate; and a nonconductor which forms a boundary between the portions of the cathode substrate and the anode substrate that are capable of contacting one another, wherein at least one of the cathode substrate and the anode substrate is a semiconductor doped with impurities and the other is a metal electrode.

Liu et al. report the use of a conductive and compatible carbon nanotube/chitosan nanocomposite as a new type of MFC biocathode material, fabricated by electrodepositing carbon nanotubes and chitosan onto a carbon paper electrode, which nanocomposite can increase electricity generation and the maximum power density of the MFC with this nanocomposite increase by 67% and 130% (Liu 2011).

Gau (U.S. patent application Ser. No. 12/154,017, filed Jun. 20, 2008, and hereby incorporated herein by reference in its entirety and made part of this application) discloses a biosensor that includes a working electrode, a reference electrode and a counter (auxiliary) electrode, and a method for confining a solution and providing controlled contact between the solutions and electrodes using controllable surface properties and surface tension forces at a small scale, the biosensor capable of sensing ionic macromolecules using a hybridization and enzyme amplification scheme to improve sensitivity.

Ringeisen et al. (Ringeisen 2007) (U.S. patent application Ser. No. 11/978,662, filed Oct. 30, 2007, and hereby incorporated herein by reference in its entirety and made part of this application) disclose a microbial fuel cell comprising a nanoporous membrane having about 100 nm to 1000 nm pore size that sequesters a microbe in the anode chamber, allowing nutrients to flow from the cathode chamber to the anode chamber and modifiable by a thin film composite (TFC) to create a TFC nanofiltration membrane.

Salguero et al. (Salguero 2011) (U.S. patent application Ser. No. 13/326,243, filed Dec. 14, 2011, and hereby incorporated herein by reference in its entirety and made part of this application) disclose a method and apparatus for increasing biofilm formation and power output in microbial fuel cells by incorporating in the anode material a three-dimensional and ordered structure filling the entire anode compartment, allowing fluid flow within the compartment and further allowing a Geobacteraceae biofilm to grow to its natural thickness of about 40 microns.

Lovley et al. (U.S. application Ser. No. 13/514,378, filed Dec. 22, 2010; Pub. No. US 20120288898; and hereby incorporated herein by reference in its entirety and made part of this application), disclose systems and methods for generating organic compounds using carbon dioxide as a source of carbon and electrical current as an energy source, including an embodiment having a reaction cell with a cathode and anode separated by a permeable membrane, the electrodes connected to a source of electrical power, and provided as a film on the cathode a bacterium that can accept electrons and convert carbon dioxide to a carbonbearing compound and water in a cathode half-reaction driven by the application of electrical current from an external source (producing compounds such as acetate, butanol, 2oxobutyrate, proponal, ethanol, and formate).

In light of the foregoing, there is a need for a cost effective and practical method, microorganism, and apparatus for utilizing the above-described sea water or salt water and for producing products, materials, and organic acid salts by other than chemical synthesis of petroleum derived feedstocks.

The principal object of the present invention is the provision of a process and/or microorganism for the production of acetic acid and its salts from carbon dioxide. A still further object of the present invention is the provision of a process for producing acetic acid from saltwater with air or a waste gas stream of $CO_2$ emission from manufactures or industry.

Yet another and more particular object of the present invention is the provision of a method, microorganism and apparatus involving continuous gaseous substrate fermentation under anaerobic conditions to accomplish the conversion of waste gas streams of certain industrial processes into useful products, namely acetic acid and its salts Acetic Acid Generation The conventional procedure for producing organic acids and organic acid salts is chemical synthesis of petroleum-derived feedstock. The rapidly escalating cost of petroleum has generated considerable interest in producing these valuable commodities by utilizing renewable or waste material as the feedstock. There is also growing concern over the massive amounts of atmospheric pollutants and greenhouse gases produced by conventional industrial processes. In many cases, $CO_2$ and other gases are discharged directly to the atmosphere, placing a heavy pollution burden on the environment. The global warming issue has captured worldwide attention. Carbon capture technology to reduce global warming problem has become an emerging technology field. In 2011, the U.S. Department of Energy announced a $41 million investment for carbon capture development alone.

However, the available techniques are mostly physical and chemical methods, which require tremendous levels of energy.

Acetic acid, a large-volume chemical product, is necessary to produce plastics, synthetic polymers, cloth, detergent, paper, vinegar, and many other important products. The annual production (10 M tons/year) is increasing, owing to high demands in developing countries. The price ($550/ton) is based on global market prices. Producing acetic acid consumes fossil fuels, which are energy-intensive and costly (Seth 2010).

The world's largest producer of virgin acetic acid is the U.S. (2.3 billion pounds in year 2000), accounting for 19% of the total world capacity. Other major contributors are China (44% of global capacity), rest of Asia (21%) and Western Europe (6%). Average growth in global consumption for the period 2009-2014 has been forecasted to be 3-4% annually (IHS, 2013).

Currently, over 80 percent of the U.S. acetic acid is produced by methanol carbonylation. However, this synthetic process requires relatively high temperatures and pressures, exotic materials of construction, and extensive safety-related equipment. The result is a high capital cost. The advantages of producing acetic acid biologically are its appropriateness for small-scale production, lower cost feed stocks, low energy membrane-based purification, and lower temperature and pressure requirements. Potential energy savings by using fermentation methods are estimated to be approximately 14 trillion Btu by 2020 from a reduction in natural gas use. Decreased transportation needs with regional plants will eliminate approximately 200 million gallons of diesel consumption, for combined savings of 45 trillion Btu. If the biological process were to include new acetic acid production, savings could include an additional 5 trillion Btu from production and 7 trillion Btu from transportation energy (Seth 2010).

Conventional Biological Fermentation Production of Acetic Acid

For most of human history, acetic acid was produced by fermentation of sugar to ethyl alcohol and its subsequent oxidation to acetic acid (Raspor and Goranovic 2008).

Genera of the Acetic Acid Bacteria

Acetic acid bacteria (AAB) comprise a large group of aerobic Gram-negative bacteria with the ability to oxidize ethanol to acetic acid (Gram-negative bacteria have an outer membrane that covers a thin sugar-protein (peptidoglycan) shell, which prevents Gram staining; whereas, Grampositive bacteria have a thick layer of peptidoglycan that a Gram stain can penetrate).

They are widely distributed in natural habitats and classified into the family Acetobacteraceae. (Sharafi 2010). These are of the Order: Rhodospirillales and Class: Alpha Proteobacteria. Members of this family are commonly used in industrial production of vinegar. AAB use substrate, such as glucose, ethanol, lactate or glycerol as energy sources. This biological route accounts for only about 10% of world production, owing to the high cost of consumption of food material, occupation of land, etc.; but, it remains important for the production of vinegar, as many food purity laws stipulate that vinegar used in foods must be of biological origin.

Most species of the genera of AAB produce acetic acid through the aerobic route and are within the genus *Acetobacter*. This genus was first introduced in 1898 with a single species, *Acetobacter aceti*. The genus *Gluconobacter* was proposed in 1935 for strains with intense oxidation of glucose to gluconic acid rather than oxidation of ethanol to acetic acid and no oxidation of acetate. The genus "*Acetomonas*" was described in 1954 for strains with polar flagellation and no oxidation of acetate. Within the AAB, ten genera of the Class Alphaproteobacteria are presently recognized and accommodated to the family Acetobacteraceae. These are: *Acetobacter, Gluconobacter, Acidomonas, Gluconacetobacter,* Asaia, Kozakia, Swaminathania, Sacchari-bacter, *Neoasaia* and *Granulibacter*. (Yamada 2008)

Anaerobic

Some bacteria that produce acetic acid through the anaerobic route are within the class Clostridia. Species of the genus *Clostridium* are all Gram-positive and have the ability to form spores. Another prior technology uses anaerobic bacteria to convert carbon monoxide, water (or hydrogen) and carbon dioxide into alcohols, acids and acid salts (See Gaddy et al., European Pat No. 0,909,328 B1, "Biological production of acetic acid from waste gases", filed Jul. 1, 1996, EP19960922632; Int'l App. No. PCT/US1996/011146; International Pub. No. WO 1998/000558, Sep. 29, 2010 published Sep. 29, 2010, and hereby incorporated herein by reference in its entirety and made part of this application). This method uses waste feedstock as raw material to reduce overall cost. However, it requires strict anaerobic conditions, which demand high operation and maintenance cost. Anaerobic bacteria which are known to convert carbon monoxide and water or hydrogen and carbon dioxide into alcohols and acids and acid salts include *Acetobacterium kivui, A. woodii, Clostridium aceticum, Butyribacterium methylotrophicum, C. acetobutylicum, C. formoaceticum, C. kluyveri, C. thermoaceticum, C. thermocellum, C. thermohydrosulfuricum, C. thermosaccharolyticum, Eubacterium limosum, C. ljungdahlii* PETC and *Peptostreptococcus productus*. Anaerobic bacteria known to produce hydrogen from carbon monoxide and water include *Rhodospirillum rubrum* and *Rhodopseudomonas gelatinosa*.

Another prior technology generates organic compounds using carbon dioxide as a source of carbon and electrical current as an energy source (U.S. application Ser. No. 13/514,378, filed Dec. 22, 2010; Pub. No. US 20120288898) as a prior art. Anaerobic microorganisms, *Sporomusa ovata* (DSM 2662), *Sporomusa silvacetica* (DSM 10669), *Sporomusa sphaeroides* (DSM 2875), *Clostridium ljungdahlii* (DSM 13528), *Clostridium aceticum* (DSM 1496), *Moorella thermoacetica* (DSM 21394), *Geobacter metallireducens* (lab collection, DSMZ 7210) etc were described as functional microorganisms in the system, which require anaerobic working and maintenance conditions, and thus leads to a higher cost.

SUMMARY

The invention further provides generally for a biological cathode composition and construction method as well as biological battery, particularly biological metal-air battery construction that can be utilized as battery with potentially longer duration, safer and friendly for environmental concerns. Embodiments of the invention further provide for systems and methods that utilize the new biocathode to convert carbon feedstock into organic chemicals at increased production efficiencies. Additional embodiments provide for Fuel cells that incorporate the new biocathode that may be more efficient at producing electrical current.

The present invention provides for methods, microorganisms and apparatus for the production of acetic acid and its salts from the waste gas streams of industrial processes such as oil refining, carbon black, coke, ammonia, and methanol production.

At least one embodiment of the invention for biological acetic acid generations provides for a system that comprises: a reaction vessel having an anode electrode and a cathode electrode disposed therein, the anode electrode having at least one surface and an anode electrical contact terminal, the cathode electrode having at least one surface and a cathode electrical contact terminal, the cathode electrode having biologically active material adjacent to at least one surface of the cathode electrode and in electrical communication therewith, the reaction vessel configured to contain a working fluid having mobile ions therein; a reaction medium in contact with the cathode electrode and the anode electrode, the reaction medium configured to contain dissolved carbon dioxide as a source of carbon; an electronic device to be able to control electrode potential at certain level; and a source of carbon dioxide configured to provide carbon dioxide to the biologically active material adjacent to at least one surface of the cathode electrode by way of the reaction medium, the system is configured with or without air flow through cathode electrode.

One embodiment of the invention for a biocathode Microbial fuel cell system, comprises a reaction vessel having an anode electrode and a cathode electrode disposed therein. Anode and cathode are isolated by an ion exchange membrane or a separation membrane. The anode electrode having at least one surface and an anode electrical contact terminal, the cathode electrode having at least one surface and a cathode electrical contact terminal, the cathode electrode having active biological material, adjacent to at least one surface of the cathode electrode and in electrical communication therewith, the reaction vessel configured to contain a working fluid having mobile ions therein; a reaction medium in contact with the cathode electrode and the anode electrode, the reaction medium configured to contain dissolved carbon dioxide as a source of carbon configured to provide carbon dioxide to the biologically active material adjacent to at least one surface of the cathode electrode by way of the reaction medium. The anode can be metal electrode or carbon electrode (graphite, carbon fiber, carbon paper, carbon cloth, carbon felt etc) has anodic bacteria grown on surface and using organic medium as substrate to supply bacteria growth. Bacteria convert organic carbon into CO2 and electricity, which flows through anode, external circuit and resistors to the cathode. Anode and cathode are connected externally through resistors and wires.

One embodiment of the invention for biocathode battery system comprises a reaction vessel having an anode electrode and a cathode electrode disposed therein, anode and cathode are isolated by an ion exchange membrane or a separation membrane. The anode electrode can be metal, such as, lithium, magnesium, zinc etc, having at least one surface and an anode electrical contact terminal, the cathode electrode having at least one surface and a cathode electrical contact terminal, the cathode electrode having biologically active material adjacent to at least one surface of the cathode electrode and in electrical communication therewith, the reaction vessel configured to contain a working fluid having mobile ions therein; a reaction medium in contact with the cathode electrode and the anode electrode, the reaction medium, configured to contain dissolved carbon dioxide and air. Carbon dioxide may serve as a source of carbon to the microorganisms; the biologically active material adjacent to at least one surface of the cathode electrode by way of the reaction medium with dissolved air.

One embodiment of the invention for biocathode fuel cell system composes a reaction vessel having an anode electrode and a cathode electrode disposed therein, anode and cathode are isolated by an ion exchange membrane or a separation membrane. The anode electrode can be metal, such as, lithium, magnesium, zinc etc, organic compounds or other compounds as fuel, having at least one surface and an anode electrical contact terminal, the cathode electrode having at least one surface and a cathode electrical contact terminal, the cathode electrode having a film of biologically active material adjacent to at least one surface of the cathode electrode and in electrical communication therewith, the reaction vessel configured to contain a working fluid having mobile ions therein; a reaction medium in contact with the cathode electrode and the anode electrode, the reaction medium, configured to contain dissolved carbon dioxide and air The air is continuously supplied through the reaction medium and the metals are consumed as fuel. the biologically active material adjacent to at least one surface of the cathode electrode by way of the reaction medium.

The invention provides further for a pure-culture, mixed-culture, aerobic or facultative microorganisms (i.e., it does not require strict anaerobic condition for growth and function) to be used in conjunction with a biocathode in a bioreactor into which $CO_2$ as a carbon source can be obtained from air (or dissolved carbon dioxide obtained from air) and introduced to the bioreactor.

One or more embodiments further provide for compatible electrode material to create a high-efficiency biocathode. One or more embodiments can provide for the highly compatible electrode material to have a particular range of "pore throat size", preferably in the range of 1-20 µm, and more preferably a pore size smaller than 2 µm and most preferably having pore throat size of 1 µm.

The invention provides further for a modifying the surface tension of one or more MFC electrodes to reduce total free energy of the system for better sorption of the microbial cells to the electrode, varying dissolved oxygen concentration in the biocathode chamber, and changing pore throat aperture on the electrodes to provide more available microbial sorption sites, to influence microbial migration and sorption on the electrode surface while remaining compatible with the flow of air and substrate to and from the cathode. At least one embodiment provides for changing the surface tension of the electrodes by treating them with hydrophobic reagents. When this is accomplished the biocathode performances is enhanced substantially. While nontreated electrodes can take 8 to 48 hours before producing electrical current, the hydrophobic pretreated biocathode electrode can produce current immediately. Hydrophilic pretreated biocathodes do not show current enhancement. A further embodiment provides for applying carbon materials, such as porous graphite block (Poco Graphite, Inc.), to the cathode having different pore throat apertures. In such an embodiment, the pore size will be preferably around 1 µm, with this pore size in this type of material corresponding to more and faster current production than similar materials with pore sizes of 10 and 20 µm.

In yet another preferred embodiment of the invention, another contact material may be used as a contact layer, such as, without limitation, a contact layer comprising carbon particles having diameters preferably in the range of 0.1 nm and 0.5 µm in diameter, and more preferably particles of 8 nm to 0.2 µm in diameter. In at least one preferred embodiment, for porous particles, the pore size within each such particle can be smaller than 2 nm (microporous particles) or between 2 nm and 50 nm (mesoporous particles). One most preferred embodiment uses a carbon particle size most preferably in the range between 8 nm and 50 nm and a pore size within the particle smaller than 2 nm.

According to embodiments of the invention, optimizing electrode surface properties and enhancing the bacteria electrode surface coverage ratio to about 80%, enables achieving 10-fold better performance without increasing the surface area of the cathode electrode.

In one embodiment of the invention, the microorganisms were deposited on the cathode electrode through applying an electric field.

In one embodiment, the active cathodic microorganisms are deposited on the surface of the electrode through either painting, brushing, coating, soaking, electric deposition or other deposition method to the support layer (electrode) in binding solution then dry. One embodiment of a coating process is through fluidised bed coating process, one or more liquid layers of coating material, bacteria culture and or carbon particle water solution or TEFLON® solution, are deposited on a solid substrate, porous electrode and subsequently dried to form solid films resulting in a homogenous coating layer of uniform thickness bacteria coated electrode. The cells are either loaded into the product basket of the granulator prior to process start or sucked into the porous when the fluidising air flow causes suction pressure. Drying processes are through either freeze drying, vacuum drying, spray drying, or fluidised bed drying.

In one embodiment, a biocathode metal-air battery cell contains a reaction vessel, anode and cathode are isolated by an ion exchange membrane or a separation membrane/material. The anode electrodes are metal, such as, lithium, magnesium, zinc, sodium, magnesium, ion, aluminum, calcium, potassium, manganese, chromium or combine of any of them. At least one surface and an anode electrical contact terminal, the cathode electrode having at least one surface and a cathode electrical contact terminal, the designed cathode electrode having biologically active material adjacent to at least one contact layer of the cathode electrode and in electrical communication through a reaction medium in contact with the cathode electrode and the anode electrode. The reaction medium is utilized as electrolyte.

In one embodiment, a biocathode fuel cell system, comprising a reaction vessel having an anode electrode and a cathode electrode, isolated by an ion exchange membrane or a separation membrane/material. The anode electrode can be metal or organic compounds as fuel, having at least one surface and an anode electrical contact terminal, the cathode electrode having at least one surface and a cathode electrical contact terminal, the cathode electrode having biologically active material adjacent to at least one contact layer of the cathode electrode and in electrical communication through a working fluid having mobile ions therein; a reaction medium in contact with the cathode electrode and the anode electrode. The reaction medium is continuously supplied or enclosed in cathode chamber and the metals are consumed as fuel in anode chamber.

BRIEF DESCRIPTION OF THE DRAWINGS

The objects and features of the invention can be better understood with reference to the drawings described below, and the claims.

FIG. 2A (is) Illustrates a side view of the abiotic components of the biocathode according to an embodiment of the present invention.

FIG. 3 (is) Illustrates a schematic view for explaining a method of using biocathode for acetic acid generation from brine as feedstock.

FIG. 4 (is) Illustrates a schematic view of a table showing comparison of the current output of the known published catholic microorganisms.

DETAILED DESCRIPTION

The Cathodic Microorganism

Figure 1:
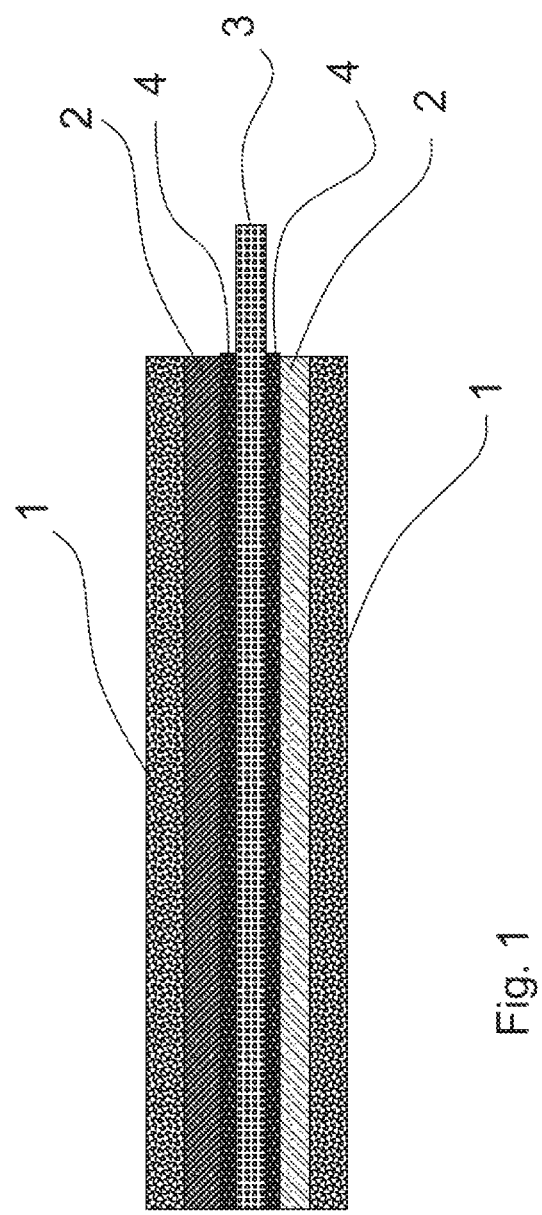
FIG. 1 (is) Illustrates a side view of all the components on the biocathode according to an embodiment of the present invention.

The invention can be described specifically and illustrated by presenting one or more preferred embodiments in the paragraphs that follow. At least one preferred embodiment of the present invention provides for incorporating into an electrode one or more strains of bacteria that can enact the conversion of carbon dioxide into useful multi-carbon compounds with higher efficiency under aerobic conditions and suitable electrochemical conditions.

In at least one embodiment, the reaction medium can be configured to contain carbon dioxide as a source of carbon and to be oxidized; a source of electrical energy, the source of electrical energy electrically connected to the cathode electrical contact terminal and to the anode electrical contact terminal; and a source of carbon dioxide to the biological material adjacent to at least one surface of the cathode electrode by way of the reaction medium.

In addition, the present invention can be used as cathode material in Microbial Fuel Cell. Modifications to the conditions can result in the generation of higher current density. The Microbial Fuel Cell can comprise a reaction vessel having an anode electrode/stack of anode electrodes and a cathode electrode/stack of cathode electrodes disposed therein. At least one embodiment of the invention provides further for an ion exchange membrane or other seperators to be placed in between the anode and cathode electrode, the cathode electrode having biologically active material adjacent to at least one surface of the cathode electrode and in electrical communication therewith, the reaction vessel configured to contain a working fluid therein; and a reaction medium in contact with the cathode electrode and the anode electrode.

Depending on the specific microorganism(s) utilized, variables to be considered in forming products include, for example, among others, without limitation: nutrient constituents and concentrations, medium, pressure, temperature, gas flow rate, liquid flow rate, reaction pH, agitation rate (if utilizing a Continuously Stirred Tank Reactor), inoculums concentration, maximum substrate (introduced gas) concentrations to avoid inhibition, and maximum product concentrations to avoid inhibition.

The present invention provides, in at least one embodiment, a process for producing acetic acid, comprising: providing a continuous flow of air and/or a gas comprising carbon dioxide into a bioreactor, said bioreactor containing anode and cathode electrode, an aqueous nutrient medium and the bacterium on the cathode side; directing a flow of the aqueous medium into the cathode side; and converting the gas in the medium using the bacterium at a pH around neutral under conditions that permit converting the gas to the acetic acid.

In one preferred embodiment the acetic acid can be recovered from the aqueous phase in a separate vessel or vessels, utilizing a suitable recovery process. Examples of recovery processes include extraction, distillation or combinations thereof, or other efficient recovery processes. The bacteria are removed from the aqueous phase and recycled to avoid toxicity and maintain high cell concentrations, thus maximizing reaction rates. Cell separation, if desired, is accomplished by centrifugation, membranous ultrafiltration, or other techniques.

The invention also provides, in an alternative aspect, one or more pure cultures of the microorganisms can be describable.

Setups of the Biological Reactor

A bioreactor having a reaction vessel with an anode electrode and a cathode electrode disposed therein, the anode electrode having at least one surface and an anode electrical contact terminal, the cathode electrode having at least one surface and a cathode electrical contact terminal, the cathode electrode having biologically active material adjacent to at least one modified surface of the cathode electrode and in electrical communication therewith, the reaction vessel configured to contain a working fluid for anode and cathode having mobile ions therein by an ion exchange membrane or a separation membrane, a reaction medium in contact with the cathode electrode and the anode electrode, the reaction medium configured to contain dissolved carbon dioxide as a source of carbon for cathode, a batch or a flow of medium into and out of the cathode side, a continuous access or supply of air into the cathode side, such that the gas mixes dissolve into the medium, and maintaining pH around neutral and maintaining other conditions appropriate for permitting the bacterium to catalyze the oxidation reaction with oxygen as electron acceptor.

In at least one preferred embodiment, a power source, such as a potentiostat, can be used to set up a three-electrode configuration during acetic acid generation (as depicted in FIG. 3). In such a configuration, the cathode can be set as the working electrode, the anode as a counting electrode and a reference electrode can be set to be close to the cathode electrode to control the working electrode (in this case the cathode electrode) at certain potential, which is desirable for the growth of the microorganisms on the electrode. In this application, the microorganisms grow on the cathode, utilize the cathode electrode as electron donor, use oxygen or chemical oxidant as electron acceptor, and may convert $CO_2$ into acetic acid and other multi-carbon compounds. The three electrodes are connected with the source of electrical energy. In one embodiment, in a 200 ml cathode chamber, 1.6 µM/s of 2butanol can be generated with negligible amount of biomass on the cathode electrode through fluorescent microscope. This yield corresponds to the input of dissolved $CO_2$ from air.

In a further embodiment, a working fluid having mobile ions therein is a source of a chemical species configured to be oxidized. In yet a further embodiment, the apparatus further comprises a control module configured to control a selected one of an electrical potential applied between the cathode electrode and the anode electrode, and an electrical current caused to flow between the cathode electrode and the anode electrode. In an additional embodiment, the apparatus further comprises a third electrode having a third electrical contact terminal in electrical communication with the control module, the third electrode configured to provide a reference potential to the cathode electrode.

Other objects and further scope of the applicability of the present invention will become apparent from the further detailed description that follows, taken in conjunction with the accompanying drawings, wherein like parts are designated by like reference numerals. The following specific examples of one or more preferred embodiments are submitted to illustrate but not to limit the present invention.

EXAMPLES

FIG. 3 illustrates an acetic acid production system and process workflow according to at least one preferred embodiment of the invention. Referring to FIG. 3, at least one of air gas and/or a gas containing carbon dioxide is introduced via influent port 1 to an influent mixing tank 3. A medium solution feedstock influent port 2 also enables such feedstock to be added to the influent mixing tank 3. The influent mixing chamber is connected by piping or other means allowing fluid connection to a bioreactor 8. The preferable range of the volume of the reactor can be from 100 ml to 30 $m^3$.

A more preferred range is between 100 ml and 1 $m^3$. The bioreactor is preferably a batch reactor or chemostat preferably at a flow rate between 1 ml/min to 100 ml/min, and more preferably a flow rate between 1 ml/min and 10 ml/min. Permeable membrane 5 is disposed within the bioreactor 8 such that two sides are created within the bioreactor on either side of the membrane 5. The membrane can be made of Nafion (Dupont) with different thicknesses, preferably at 1, 2, 5, or 7 mils. A more preferable thickness is 1 or 2 mils. Alternatively, in another embodiment a filtration membrane can be used, preferably with a pore size smaller than 1 µm, and more preferably below 100 nm. The filtration membrane can be made of Acrylic Copolymer (AC), PES, PVDF, PTFE, MCE, Nylon, PP, CACN and GF. Preferably the membrane is of Nafion, PTFE. The membrane is sealed tight in between the anode and cathode, e.g., configured as a Membrane Electrode Assembly (MEA), or it can be positioned separately in between anode and cathode electrode and sealed tight against the wall of the bioreactor. Liquid is able to flow through the membrane; ions and/or small molecules are exchangeable through the membrane depending on the type of membrane (e.g., an Anion Exchange Membrane allow exchange of anions and a Cation Exchange Membrane allow exchange of cations). A filtration membrane allows a smaller size of molecule to pass through). The configuration can be that the membrane is positioned in between anode and cathode electrodes separately or as a Membrane Electrode Assembly (MEA). For acetic acid production, the electrodes and membrane separated configuration is preferred. The distance between membrane and electrode varies according to the volume of the reactor. For MFC, the configuration of a Membrane Electrode Assembly is preferred. On one side of the membrane, anode 7 is positioned, thus creating the anode side of the bioreactor, while on the other side of the membrane is positioned a biocathode 6, thus creating the biocathode side of the bioreactor.

For both cases, anode and cathode electrodes are preferred to be configured with the same size facing to each other with the membrane constructed in the middle. The preferred size of the electrode is according to the volume of the reactor. For example, in a 30.8 $m^3$ reactor the size of electrode and membrane is preferably about 3.35 m×3.35 m. An electrical power system 11 (such as, for example, without limitation, a potentiostat) is connected by wiring to a reference electrode 4 (e.g., Ag/Agcl electrode, Zinc reference electrodes, Minitek reference electrodes, Alutek reference electrodes, preferably Ag/AgCl reference electrode (Cathelco Ltd)) and to the anode 7.

Continuing to refer to FIG. 3, a distillation or extraction tank 12 is connected by piping or other means to the bioreactor 8. Tank 12 is extraction, distillation tank or combinations thereof or repeat as an efficient recovery processes. Chemicals can be added into tank 12 to assist separation, such as solvent. The effluent solution can be mixture of chemical compounds. The distillation tank is preferred because these chemicals can be separated according to their boiling point, although secondary distillation can be used to complete separation. One example of such a vendor is Saroj Technocrats Private Limited. If by extraction, the desired extraction tank of extraction equipment is mainly composed of extracting tank, condenser, cooler, oil-water separator, foam breaker, filter, and control box. The agitator can be equipped for dynamic extraction and processes under conditions of normal pressure, positive pressure, forced circulation, or hot reflux. Preferably positive pressure is used (example vendor is Zhe Jiang Sunny Machinery Technology Co., Ltd.).

Effluent water can be released via effluent water outlet 13, and can be controlled at normal pressure with valves. A separation and purification tank 9 can be attached by piping or other means to the extraction tank 12. At tank 9, the product can be further purified with less water content (one example vendor can be distillation columns and absorption columns from Titanium Fabrication Corporation). Pumps can be added at influent and effluent tank, as well as between each tank if necessary to assist liquid transportation.

Cooling is preferred for the safety of transportation. Cooling tank 10 is connected by piping to separation tank 9. Cooling is preferred to a temperature lower than 30° C. Stainless steel of ASTM 316 or 321 grade or equivalent is suitable for cooling and storage of all grades of acetic acid and its salts. The material of tanks and pipes are preferably stainless steel. In some embodiments, aluminum of minimum 99.5% purity can be used for the storage of glacial acetic acid. The temperature control of the acid must be more precise when aluminum is used rather than stainless steel, since above 30° C. the corrosion rate increases sharply, with the formation of aluminum acetate. A product collection port can be connected to the cooling tank 10, or in some embodiments can be connected directly to the purification tank 9, or to the distillation tank 12, and a transportation or storage port 14 enables product to be removed to a transportation vehicle or another storage venue, such as storage tank as mentioned above.

Figure 2B:
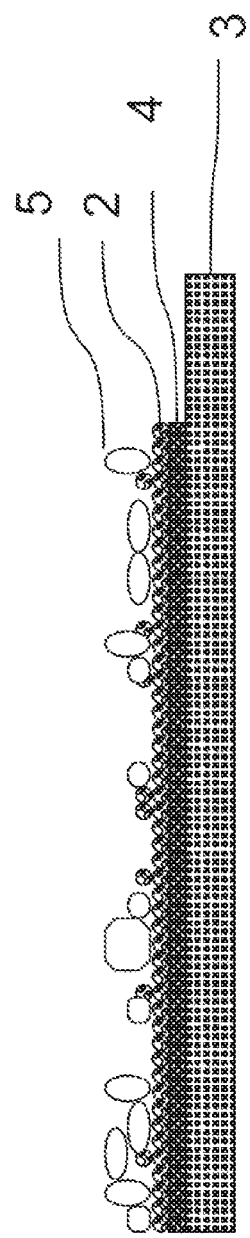
FIG. 2B illustrates the interrelationship between biological components and abiotic components on the biocathode according to an embodiment of the present invention.

In accordance with an exemplary embodiment of the present invention and as shown in FIG. 3 of the drawings, a first step in the conversion process is the preparation of influent feedstock of nutrient media for the bacteria. The content of the nutrient media will vary based on the type of bacteria utilized (such as, for example, without limitation, with bacteria *Clostridium ljungdahii*, a fresh water media can be used). The nutrients are constantly fed to an influent feedstock tank 3. The biological reactor 8 consisting of one or more vessels and/or towers of a type which includes the Continuously Stirred (CSTR), Immobilized Cell (ICR), or other suitable reactor. Within the bioreactor 8 resides the culture, either single or mixed species, of bacteria utilized in the gas conversion process. The bacteria adhere to an internal packing medium. This packing medium preferably provide maximal surface area, high mass transfer rate, low pressure drop, even gas and liquid distribution, and preferably minimize plugging, fouling, nesting and wall channeling. One example of such medium materials is the biocathode material as shown in FIG. 1 and FIGS. 2A and 2B and as described in this specification in reference thereto. FIG. 1 illustrates the overall side view of the biocathode. FIG. 2A and FIG. 2B illustrat the side view of the electrode before and after deposition of biological components.

The carbon dioxide/air gases 1 are continuously introduced into the feedstock mixing tank 3. The gas is preferably retained in the bioreactor 8 at normal pressure or higher pressure for maximizes efficiency of the process. In one embodiment, normal pressure is preferred for maintaining pressure in the system consistent.

In the biological reactor 8, bacteria inoculums are mixed with influent feedstock. Bacteria cells attach on and obtain electrons from the cathode electrode through augmentation during polarization at desired potential. In the reactor, a reference electrode is placed near the cathode. Cathode, anode and reference electrodes are connected with power source, such as a potentiostat (such as available from Gamry Instruments, Warminster, Pa.). For different microorganisms, the poise potential is different. For example, a poise potential for *Geobacter sulfurreducens*, KN400 is −400 mV. Under different operation conditions in other embodiments of the inventions, the preferred poise potential for the microorganism may vary.

Acetic acid (and/or its salt solutions) is generated in the cathode side of the bioreactor 8 and can flow into the distillation and extraction tank through a pump at flow rates between 0.1 ml/min and 10 ml/min, preferably at 0.5 ml/min. Higher flow rates can be used as needed to replace or discharge the batch solution after a period of time for batch mode. Pumps in the system can be present to assist constant flow rate when the system is set at chemostat mode. At cooling tank 10, purified acidic acid or its salts will be cooled and condensed by water. The temperature will be controlled at below 30° C., preferably at room temperature. Then it will be collected and transported through port 14 and 15. For example collected and transport using stainless steel storage tank (Northeast Fluid Control, Inc.).

FIG. 1 and FIGS. 2A and 2B show the configuration and details of a biocathode according to one or more preferred embodiments of the invention. Referring to FIG. 1, at least one embodiment of the invention provides for a biocathode constructed by outer layers of microorganisms 1 attached to contact layers 2 that are on top of binding layers to either side of conductive support layer 3. The support layer 3 can extrude to a sufficient degree to serve as an electrical contact or electronic connector.

Referring to FIG. 2A, additional detail is provided for at least one preferred embodiment of the invention, wherein construction of one side of a biocathode is illustrated, comprising conductive support substrate 3 (also termed conductive support layer 3, herein), which support layer 3 can be carbon paper, carbon cloth, carbon felt, carbon wool, carbon foam, graphite, porous graphite, a conductive polymer, platinum, palladium, titanium, gold, silver, nickel, copper, tin, iron, cobalt, tungsten, and stainless steel. The material of the conductive support layer 3 is preferably carbon paper or carbon cloth. The main components of a binding layer 4 placed adjacent to the support layer 3 can be TEFLON®, PTFE, or Nafion®. With TEFLON® PTFE the binding layer 4 is hydrophobic, with Nafion®, it is hydrophilic. The binding layer 4 can be only one of the main components or with other binders, such as a poly (butyl acrylate) polymethacrylate copolymer, a poly (vinyl alcohol), and a poly (ethylene oxide). It is preferably without the other binders. The thickness of the binding layer 4 is preferably less than 3 μm, and the concentration of the binding components in preparation is preferably between 0 to 60% by weight in water or solvent, preferably using water. More preferably, the concentration range by weight in water is between 0 to 25%, and even more preferably it is 10% by weight. The binding layer 4 can be deposited on/in support layer 3 through painting, brushing, coating, soaking the support layer in binding solution then dry. A heating procedure will be applied after the deposition procedure to remove water or solvent if applied. One example is heating to temperature of 400° C. until water or solvent are evaporated and removed. The embedding of binding molecule inside of the support layer material is preferred for better attachment of the contact layer and microorganisms.

Still referring to FIG. 2A, a contact layer 2 is placed adjacent to the binding layer 4, such that the binding layer 4 binds the contact layer 2 to the conductive support layer 3. In one or more preferred embodiments of the invention contact layer 2 can comprise a carbon material, such as, for example, without limitation, porous graphite block (Poco Graphite, Inc.), which is bound to the cathode support layer 3 with various binding materials of binding layer 4. In such embodiments, the contact layer 2 can have different pore throat apertures. In such embodiments, the pore size will be preferably around 1 µm, with this pore size in this type of material corresponding to more and faster current production than similar materials that may have pore sizes of 10 and 20 µm.

In at least one even more preferred embodiment of the invention, referring still to FIG. 2A, one or more layers of particles comprise contact layer 2, covering the entire surface of the support layer 3. The particles of contact layer 2 can be porous or non-porous. Preferably they are distributed uniformly. The material of the particle can be any conductive particles including but not limited to carbon black, porous carbon particles, conductive polymer particles, porous graphite particles, active carbon, conductive nanoparticles, graphene, carbon aerogel etc, or a combination of particles of different material. In one preferred embodiment, the particles are preferably carbon black (Cabot Corporation). These particles can be porous or non-porous. The particle size is preferably between 0.1 nm and 0.5 µm, more preferably in the range of 8 nm to 0.2 µm, and most preferably in the range of 8 nm to 50 nm. For porous particles, the typical pore size within each particle can be smaller than 2 nm (microporous particles) or between 2 nm and 50 nm (mesoporous particles). One most preferred embodiment of the invention uses a carbon particle size preferably in the range between 8 nm and 50 nm, these particles each having a typical pore size within the particle smaller than 2 nm. The particles can be made into particle ink solution to be deposited on the binding layer 2. The ink solution contains the particles, water, binder, or solvent. Loading of particles on the layer 2 depends on the property of the particles and material of the support layer 3. One example is using carbon black as particle on carbon paper with loading of 4.5 mg/cm$^2$. Another example is using carbon black as particle on carbon cloth with loading of 5.5 mg/cm$^2$. The ink solution is preferably mixed completely and uniformly. Examples of mixing methods including stir heat agitation, sonication. The ink solution can be loaded on contact layer 4 through vacuum deposition, screen print, paste, brush, spray, rolling, heat press, or methods combine any of them. The electrode is preferably heated to high temperature, such as 400° C. and then cooled down to room temperature. Solvent, such as a poly (butyl acrylate) polymethacrylate copolymer, a poly (vinyl alcohol), and a poly (ethylene oxide), without limitation, may be added into the ink if necessary. One embodiment can use carbon paper as a support layer, depositing the particle ink with 15% TEF and loading 5 mg/cm$^2$ particles on binding layer 2 through vacuum deposition and heat pressing to fix the layer, then placing in oven and gradually increasing temperature to 400° C. for 20 min., then cooling to room temperature.

Referring now to FIG. 2B, in at least one preferred embodiment of the invention, the contact layer 2 is in direct contact with a layer of microorganisms or biological material 5. A layer of microorganisms or biological material 5 will be attached onto the contact layer 2 in a configuration that depends upon the conditions of the bio-reactor. In one embodiment, the bacteria cells attached on contact layer can be through natural augmentation. Binding layer 4, contact layer 2 and microorganism or biological material layer 5 depicted in FIG. 2B can be replicated on both sides of conductive support layer 3, as is shown in FIG. 1.

In FIG. 1, a layer of micro-organisms is shown as layer 1, attaching to contact layer 2. The function of the conductive support layer 3 is to support the electrode and facilitate the electron transport of the electrode. It can be made of electron conductive material, as described above. The thickness of the support layer 3 is preferred to be between 4 and 20 mils. More preferable it is 14.5 mils. In one example of one embodiment, this material is carbon paper. One end of the conductive support layer connects with electronic wires for current transport to external devices, such as potentiostat.

Still referring to FIG. 1, upon contact layer 2, microorganisms or biological material in layer 1 can be accumulated through augmentation on the poised electrode in the system, natural dispersion, diffusion or shaking assisted uniform distribution etc.

In the processes described hereinabove and depicted in FIG. 3, the pressure at influent gas mixing tank 3 is at 1 atmosphere or higher, in order to have a higher amount of carbon dioxide dissolved in the influent salt medium. In one example, tank 3 is at 1 atmosphere and in another example the pressure is at 1.5 atmospheres.

Still referring to FIG. 1, upon contact layer 2, bacteria cells in layer 1 can also be deposited through augmentation on the poised electrode, panting, brushing, coating, soaking, filtering, pressing, and solidifying. In one embodiment of the invention, the microorganisms were deposited on the cathode electrode through applying an electric field.

In one embodiment, the active cathodic microorganisms/biological material are deposited on the surface of the electrode through either painting, brushing, filtering, flow through, vacuum pressing, coating, soaking the support layer (electrode) in binding solution then dry. One embodiment of a coating process is through fluidised bed coating process, one or more liquid layers of coating material, bacteria culture and carbon particle water solution or TEFLON® solution, are deposited on a solid substrate, porous electrode and subsequently dried to form solid films resulting in a homogenous coating layer of uniform thickness bacteria coated electrode. The cells are either loaded into the product basket of the granulator prior to process start or sucked into the porous when the fluidising air flow causes suction pressure. Drying processes are through either freeze drying, vacuum drying, spray drying, or fluidised bed drying. Protective mechanisms are applied to the microorganisms before drying to preserve their viability during drying and storage process. The protection agents added including sugar and sugar derivatives, such as cryoprotective sugars (trehalose, lactose, sucrose, glucose, maltose), borate ions, and antioxidants, such as ascorbic acid, Ammonium Compounds.

Referring again to FIG. 3, in one embodiment, it is preferred that in tank 3 the pH level is close to neutral, i.e., pH 7.0. Influent feedstock gas can be pure carbon dioxide gas or air. The pure high concentration of carbon dioxide discharged from carbon industry or other industry as "waste gas" or "waste gas streams" typically released or exhausted to the atmosphere. As shown in FIG. 3, in the influent mixing tank, the temperature and pressure can be set at room temperature and normal pressure or higher. Higher temperature or pressure can be applied for higher solubility of carbon dioxide in the solution. But the influent solution is preferably cooled down to lower than 45° C. before feeding into the biological reactor. Accordingly, the processes of the present invention are suitable for converting the atmospheric or industry carbon dioxide pollutants into useful products, namely acetic acid and other compounds.

In one embodiment, a biocathode metal-air battery cell contains a reaction vessel having an anode electrode and a cathode electrode disposed therein, anode and cathode are isolated by an ion exchange membrane or a separation membrane. The anode electrode can be metal, such as, lithium, magnesium, zinc, sodium, magnesium, ion, aluminum, calcium, potassium, manganese, chromium, having at least one surface and an anode electrical contact terminal, the cathode electrode having at least one surface and a cathode electrical contact terminal, the biological cathode electrode having biologically active material adjacent to at least one of the contact layers of the cathode electrode and in electrical communication therewith, the reaction vessel configured to contain a working fluid having mobile ions therein; a reaction medium in contact with the cathode electrode and the anode electrode, the reaction medium, configured to contain dissolved carbon dioxide and air. Carbon dioxide may serve as a source of carbon to the microorganisms; the biologically active material adjacent to at least one contact layer of the cathode electrode by way of the reaction medium.

In one embodiment, a biocathode fuel cell system, comprising a reaction vessel having an anode electrode and a cathode electrode disposed therein, anode and cathode are isolated by an ion exchange membrane or a separation membrane. The anode electrode can be metal, such as, lithium, magnesium, zinc, sodium, magnesium, ion, aluminum, calcium, potassium, manganese, chromium, organic compounds or other compounds as fuel, having at least one surface and an anode electrical contact terminal, the cathode electrode having at least one surface and a cathode electrical contact terminal, the cathode electrode having biologically active material adjacent to at least one surface of contact layer of the cathode electrode and in electrical communication therewith, the reaction vessel configured to contain a working fluid; a reaction medium in contact with the cathode electrode and the anode electrode, the reaction medium, configured to contain dissolved carbon dioxide and air. The air is continuously supplied and the metals are consumed as fuel. Carbon dioxide may serve as a source of carbon to the microorganisms; The biologically active material adjacent to at least one contact layer of the cathode electrode by way of the reaction medium.

The Comparison of the Biocathode Materials

TABLE 1

Comparison of the current output of aerobic facultative biocathode.

| Source | Current dens. (A/m2) | Duration (day) | Cathode Material | Polarization method | Culture | LPP v. SHE (V) |
|---|---|---|---|---|---|---|
| 1. | 0.46 nc | 12 | SS | CP | MC | −0.156 |
| 2. | 0.6 nc | na | GF | CP | MC | −0.001 |
| 3. | 0.37 v. c | not ind | SS | PC | PC | −0.32 |
| 4. | 0.50 nc | not ind | SS | PC | PC | −0.001 |
| 5. | 0.92 v. c | >11 | GR | CP | PC | −0.351 |
| 6. | 7.5 v. c | >11 | CM | CP | PC | −0.351 |
| 7. | exp > 7.5 v.c. | >11 | CPM | CP | PC | −0.351 |

Where sources are
1. Bergel et al., 2005;
2. Erable B., Bergel et al., 2010;
3. Rabaey et al., 2008;
4. Vandecandelaere et al., 2008;
5. Zhang, P., et al, 2011 (manuscript);
6. Zhang, P., 2012;
7. Zhang, P., et al (pending).
Current density:
nc = no control;
v.c. = versus control.
Cathode material:
SS = stainless steel,
GF = graphite felt (no collector),
GR = Graphite Rod,
CM = Carbon material,
CPM = Compatible material.
Polarization method:
CP = Constant Polarization,
PC = Polarization curve (1mV/s).
Culture:
MC = Mix culture,
PC = Pure culture.
LPP = lowest polarization potential.

Bacteria that can be Used in Various Embodiments

Anaerobic bacteria which are known to convert carbon monoxide and water or hydrogen and carbon dioxide into alcohols and acids and acid salts include *Acetobacterium kivui, A. woodii, Clostridium aceticum, Butyribacterium methylotrophicum, C. acetobutylicum, C. formoaceticum, C. kluyveri, C. thermoaceticum, C. thermocellum, C. thermohydrosulfuricum, C. thermosaccharolyticum, Eubacterium limosum, C. ljungdahlii* PETC and *Peptostreptococcus productus. Acetobacterium woodii* and *Acetoanaerobium noterae* produce acetate from $H_2$ and $CO_2$, but, in addition to acetate, *A. noterae* produces some propionate and butyrate. Another chemolithotrophic bacteria, *Clostridium aceticum*, produces acetate from $CO_2$ using a glycine decarboxylase pathway.

By mixed strains, it is meant a mixed culture of two or more bacteria. This mixed strain, when utilized in the process described herein, produces acetic acid under aerobic or anaerobic conditions. It may also be applied to biocathode utilized to produce other organic acids or salts thereof, alcohols, hydrogen, SCP or other product, such as electricity etc.

In the development of the present invention, new strains of facultative bacteria have been isolated which cause this conversion with high efficiency as compared to other known bacteria as shown in Table 1 (and FIG. 4). The microorganism is active under either aerobic or anaerobic conditions. Depending on the specific microorganism(s) utilized, variables which must be considered in forming products from waste carbon dioxide gas include nutrient constituents and concentrations, medium, pressure, temperature, gas flow rate, liquid flow rate, reaction pH, agitation rate (if utilizing a Continuously Stirred Tank Reactor), inoculum level, maximum substrate (introduced gas) concentrations to avoid inhibition, and maximum product concentrations to avoid inhibition.

Advantages and Benefits of the Invention

Thus, it will be appreciated that as a result of the present invention, a high efficient, cost effective, biological cathode electrode material provides board applications in acetic acid generation, enhancing performance of microbial fuel cell, metal-air battery, fuel cell etc.

Thus, as a result of the present invention, a highly effective improved process for converting carbon dioxide to acetic acid, oxalic acid, 2-oxobutyrate or its salts is provided by which the principal objective, among others, is completely fulfilled.

In accordance with the present invention it is now possible to produce valuable acetic acid and acetate salts, oxalic acid, 2-oxobutyrate, not only reducing consumption of valuable chemical feedstock, but also removing hazardous atmospheric pollutants from the carbon dioxide gas streams of industries. Previous processes to derive these chemicals biologically were based on fermentation of sugars.

The cultivation and operational cost of the invention is lower with broader application and commercialization potential.

In accordance with the present invention, acetic acid and other useful compounds are (is) produced from the biological consumption of carbon dioxide, thereby reducing environmental global warming gas content, at the same time saving energy and chemical feedstock.

MFC as a renewable energy technique, if it can be scaled up for commercialization, will generate tremendous revenue for multiple industries. Today, more than 16,000 municipal wastewater treatment facilities (WWTFs) are in operation in the United States. Total cost of electricity bill of WWTFs is about 4 billion dollars per year. An enhanced cathode according to the invention makes the MFC an ideal technology for BOD removal and renewable bioenergy generation for wastewater treatment plant. Also, for the $1.5 billion marine underwater power supply market, there is a need to have more sustainable and less toxic power supply solution. An embodiment of an enhanced biocathode according to the invention can continuously generate energy in long term without toxicity issues. With such a biocathode, having 10 times higher performance than before enhancement and 40 times better performance than carbon electrode, the commercialization of Bio-cathode MFC in multiple industries is possible. MFC as a clean energy technique will benefit the sustainable development of our society in long run.

According to a 2005 estimate, the worldwide battery industry generates US$48 billion in sales each year, with 6% annual growth. The global metal air batteries market is expected to grow to nearly $1.7 billion by 2018, with a five-year compound annual growth rate (CAGR) of 31%. Hearing aid devices, the fastest-growing segment, is moving at a steady 3.7% CAGR. In 2012, the fuel cell and hydrogen energy industry was expected to produce $785 million in revenue, according to Pike Research.

It is contemplated and will be apparent to those skilled in the art from the preceding description and accompanying drawings that modifications and/or changes may be made in the illustrated embodiments without departure from the present invention. Accordingly, it is expressly intended that the foregoing description and accompanying drawings are illustrative of preferred embodiments only, and are not limiting, and that the scope of the present invention be determined by reference to the appended claims.

What is claimed is:

1. A biological battery system, comprising:
    a reaction vessel, configured to retain therein an aqueous medium containing a microorganism culture;
    a biological cathode electrode, disposed in the reaction vessel, having no metallic catalyst, and including:
        a conductive support layer including a composition selected from the group consisting of carbon, a polymer, and combinations thereof;
        a contact layer disposed on the conductive support layer and including carbon particles, the carbon particles having a size ranging between 0.1 nm and 500 nm, the contact layer being configured to be in electrical contact with the aqueous medium when the aqueous medium is retained in the reaction vessel; and
        a polymeric binding layer disposed between the conductive support layer and the contact layer, the polymeric binding layer configured to cause adhesion of the contact layer to the conductive support layer while still preserving conductivity between the contact layer and the conductive support layer; and
    a conductive anode disposed in the reaction vessel,
    wherein when in operation the reaction vessel is open to an ambient air such that air is supplied to the microorganism culture and wherein the microorganism culture accepts electrons from the cathode.

2. The biological battery system of claim 1, wherein oxidation at the anode is not mediated by the microorganism culture.

3. The biological battery system of claim 1, wherein no anion or cation selective barriers are in the reaction vessel.

* * * * *